(12) United States Patent
Cohen

(10) Patent No.: US 7,043,308 B2
(45) Date of Patent: May 9, 2006

(54) SURFACE ELECTRODE FOR ELECTRICAL STIMULATION OF TISSUE

(75) Inventor: Shlomi Cohen, Tel-Aviv (IL)

(73) Assignee: Stimu-Heal, Inc., Tel Aviv (IL)

( * ) Notice: Subject to any disclaimer, the term of this patent is extended or adjusted under 35 U.S.C. 154(b) by 497 days.

(21) Appl. No.: 10/367,920

(22) Filed: Feb. 19, 2003

(65) Prior Publication Data
US 2004/0162602 A1   Aug. 19, 2004

(51) Int. Cl.
*A61N 1/04* (2006.01)
(52) U.S. Cl. .................. 607/152; 607/142; 607/149
(58) Field of Classification Search ............. 607/142, 607/144, 149, 152
See application file for complete search history.

(56) References Cited

U.S. PATENT DOCUMENTS

| | | | |
|---|---|---|---|
| 4,398,545 A | 8/1983 | Wilson | 607/152 |
| 4,559,950 A | 12/1985 | Vaughan et al. | 600/394 |
| 4,574,809 A | 3/1986 | Talish et al. | 607/27 |
| 4,787,390 A * | 11/1988 | Takata | 600/396 |
| 4,998,532 A | 3/1991 | Griffith | 607/2 |
| 5,309,909 A | 5/1994 | Gadsby et al. | 600/386 |
| 5,520,180 A * | 5/1996 | Uy et al. | 600/397 |
| 6,115,625 A * | 9/2000 | Heard et al. | 600/391 |
| 6,148,233 A * | 11/2000 | Owen et al. | 607/5 |
| 6,321,119 B1 | 11/2001 | Kronberg | 607/66 |
| 2002/0016618 A1 | 2/2002 | Da Silva et al. | 607/72 |
| 2002/0117408 A1 | 8/2002 | Solosko et al. | 206/210 |

* cited by examiner

Primary Examiner—Carl Layno
(74) Attorney, Agent, or Firm—Mark M. Friedman

(57) ABSTRACT

A surface electrode for long-term delivery of an electrical signal to a skin surface of a patient, the surface electrode including: (a) a flexible, at least partially-conductive surface layer for physically contacting the skin surface, and for delivering thereto the electrical signal, and (b) an electrically conductive layer, operatively connected to the partially-conductive surface layer, for transferring the electrical signal thereto, wherein the at least partially-conductive surface layer has a thickness of less than 0.5 mm, and preferably contains a conductive gel or artificial skin.

38 Claims, 4 Drawing Sheets

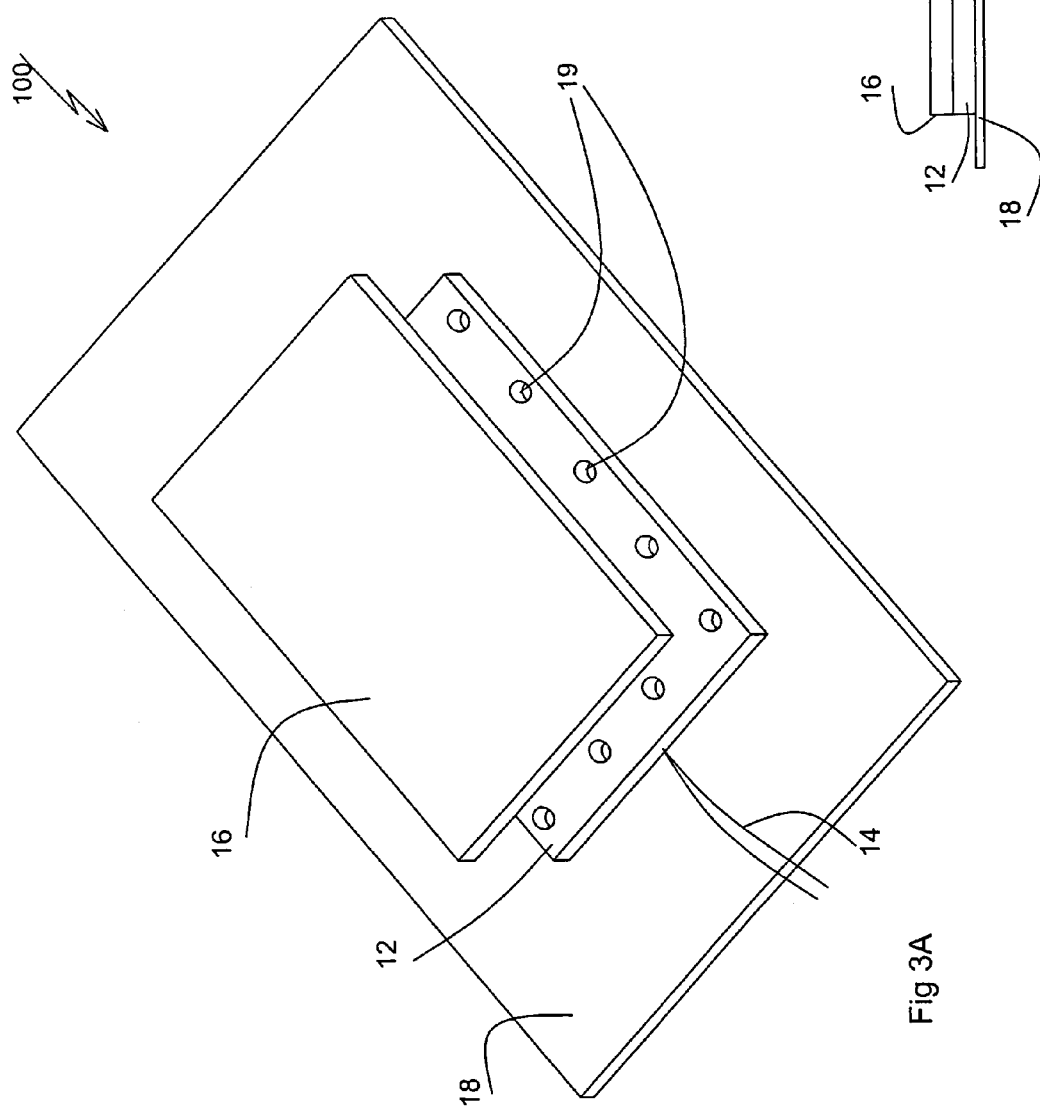

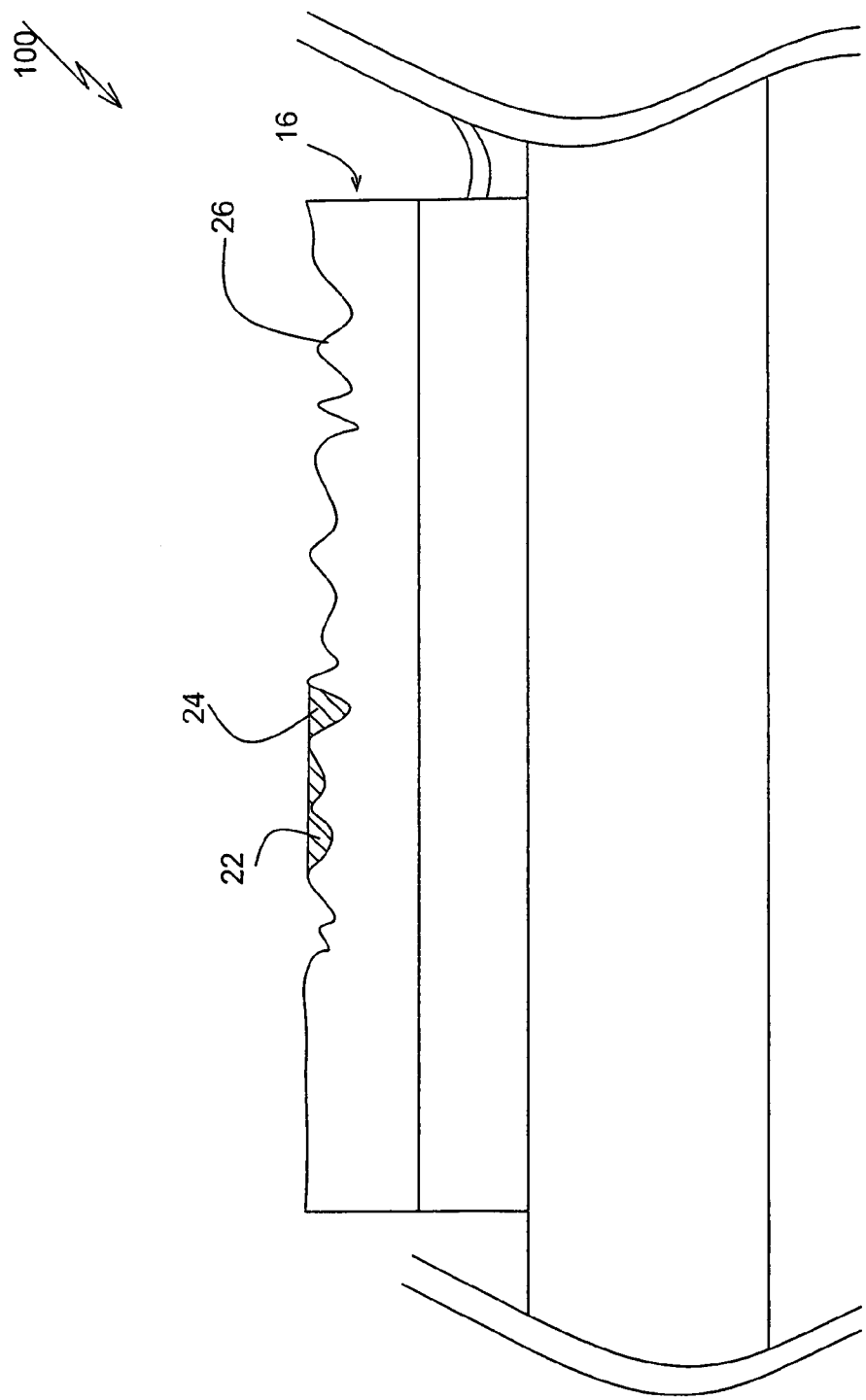

SURFACE ELECTRODE FOR ELECTRICAL STIMULATION OF TISSUE

FIELD AND BACKGROUND OF THE INVENTION

The present invention relates to stimulation using electrical impulses and, in particular, to a system and method of providing electrical stimulation via the skin of a patient, by means of an inventive surface electrode.

Electrodes which are used to deliver electrical stimulation through the surface of the skin generally require the use of a conductive liquid or solid gel, often termed "hydrogel", to provide a continuous conductive path between the skin and the current source. Conductive gels contain a salt (typically KCl or NaCl) in order to achieve the requisite electrical current flow. The preferred gel is one with a high salt content, since such a gel produces a better conductor than that obtained when using a gel with a low salt content. In addition, the use of a high salt content gel typically requires less skin abrasion at the time of application to reduce the impedance of the skin-electrode interface after subsequent electrode application.

For ease of use, it is desirable to apply the conductive liquid or solid gel at the point of manufacture, creating a "pre-gelled" electrode. U.S. Pat. No. 4,559,950 issued to Vaughn and U.S. Pat. No. 5,309,909 issued to Gadsby describe such electrodes. Pre-gelled electrodes save the step of manually applying the gel to the electrode at the time of electrode application and speed the application process considerably.

Known gels are typically hydrophilic, to improve conductivity of the gel, and perhaps more importantly, to slow the gradual dehydration of stored, sealed electrodes. It is reported by U.S. patent application No. 20020117408 to Solosko, et al., that the shelf life of an electrode pad is largely determined by the length of time it takes for enough water moisture to evaporate out of the hydrogel and escape the package of the pad. It is further articulated that as moisture escapes from the packaging, the electrical properties of the electrode pads become increasingly compromised.

This problem is a critical one for numerous and varied medical applications. For example, when electrode pads are utilized with a defibrillator, a very significant factor includes changes in small and large signal impedance values between a patient and a defibrillator. As the hydrogel dries out, the impedance values increase, making it more difficult to monitor electrical signals from the patient, obtain transthoracic impedance, and deliver energy into the body.

Water loss can affect the mechanical properties of the hydrogel as well. In some hydrogels, the loss of water causes the hydrogel to skin over or solidify, especially around the edges, which inhibits the ability of the hydrogel to adhere to the skin. This partial or complete loss of adhesion can render an electrode useless since it cannot then create or maintain an effective contact with the patient's skin. Thus, water loss from the electrode pad can prevent or attenuate receipt of electrocardiogram (ECG) signals by a defibrillator. In addition, water loss from the electrode pad can alter the delivery of defibrillation energy from a defibrillator to the patient.

Additionally, poor or uneven contact of the electrode pad with the skin of a patient may unduly concentrate energy transfer during defibrillation into areas that exhibit good skin contact. Higher than usual current densities resulting from poor or uneven skin contact can cause skin burns. If the current is not delivered to a patient in the manner for which the electrode pad was designed, the resulting treatment delivered to the patient may be altered, compromising patient outcome.

Although highly hydrophilic hydrogels slow the gradual dehydration of stored, sealed electrodes, and also slow the gradual dehydration of electrodes on most exposed skin surfaces, the changes in mechanical and electrical properties over the long term, exceed the tolerances in many medical applications. Moreover, highly hydrophilic gels have distinct disadvantages in applications requiring long-term, "wet" contact between electrode and skin, e.g., in a closed environment underneath a cast. In such wet environments, hydrophilic gels absorb water and/or sweat on the skin surface, causing swelling and even disintegration of the conductive pad.

There are several known devices for electrical stimulation of injured tissue situated underneath a cast. U.S. Pat. No. 4,574,809 to Talish, et al., entitled "Portable Non-Invasive Electromagnetic Therapy Equipment", teaches a cast-embeddable coil structure which includes a single connector fitting, designed for exposure externally of a completed cast and for removable mounting and electrical connection to a self-contained portable signal-generator unit. The signal-generator unit is mounted to the cast only for periods of therapeutic treatment, and is removably mounted to a less-portable charging unit in intervals between periods of therapeutic treatment. Similarly, U.S. Pat. No. 4,998,532 to Griffith, entitled "Portable Electro-Therapy System", teaches a portable non-invasive apparatus for electro-therapeutic stimulation of tissue and bone healing, worn or carried by a patient. U.S. Pat. No. 6,321,119 to Kronberg, entitled "Pulsed Signal Generator For Bioelectric Stimulation And Healing Acceleration", teaches a pulsed signal generator for various biomedical applications, including electrical stimulation of fracture healing, treatment of osteoporosis, strengthening of freshly-healed bone after removal of a cast or other fixation device, and iontophoresis. U.S. patent application No. 20020016618 to Da Silva, et al., entitled "Integrated Cast And Muscle Stimulation System", teaches a device that allows electrical stimulation to an anatomical site that is covered by a cast. The electrode is applied to achieve a desired physiological response (e.g., bone growth), treatment of pain, or the prevention of muscle atrophy.

Electrical stimulation treatments of injured tissue situated underneath a cast typically last 3–6 weeks, and may be significantly longer in some cases. Hence, all such systems would benefit from an electrode in which the mechanical and electrical performance is sustained, even under the harsh conditions beneath the surface of the cast.

It would be highly advantageous, therefore, to have a surface electrode for electrical stimulation of tissue having sustained mechanical and electrical performance over long-term storage and use, so as to enable transcutaneous electrical communication in a safe, reliable, and effective manner, even under difficult topical and ambient conditions.

SUMMARY OF THE INVENTION

The present invention is a surface electrode for electrical stimulation of tissue, the electrode having sustained mechanical and electrical performance over long-term use.

According to the teachings of the present invention there is provided a surface electrode for long-term delivery of an electrical signal to a skin surface of a patient, the surface electrode including: (a) a flexible, at least partially-conductive surface layer for physically contacting the skin surface, and for delivering thereto the electrical signal, and (b) an electrically conductive layer, operatively connected to the partially-conductive surface layer, for transferring the electrical signal thereto, wherein the at least partially-conductive surface layer has a thickness of less than 0.5 mm.

According to another aspect of the present invention there is provided a surface electrode for long-term delivery of an electrical signal to a skin surface of a patient, the surface electrode including: (a) a flexible, at least partially-conductive surface layer for physically contacting the skin surface, and for delivering thereto the electrical signal, and (b) an electrically conductive layer, operatively connected to the partially-conductive surface layer, for transferring the electrical signal thereto, wherein the at least partially-conductive surface layer includes an artificial skin.

According to further features in the described preferred embodiments, the at least partially-conductive surface layer is bio-compatible.

According to still further features in the described preferred embodiments, the at least partially-conductive surface layer has a thickness of 0.05–0.35 mm.

According to still further features in the described preferred embodiments, the at least partially-conductive surface layer has a thickness of less than 0.25 mm.

According to still further features in the described preferred embodiments, the at least partially-conductive surface layer has a thickness of 0.08–0.25 mm.

According to still further features in the described preferred embodiments, the at least partially-conductive surface layer is a gel.

According to still further features in the described preferred embodiments, the electrically conductive layer includes a metal foil.

According to still further features in the described preferred embodiments, the at least partially-conductive surface layer includes artificial skin.

According to still further features in the described preferred embodiments, the at least partially-conductive surface layer is sufficiently pliable so as to fill pores in the skin surface.

According to still further features in the described preferred embodiments, the surface electrode further includes: (c) an adhesive bandage, operatively connected to the electrically conductive layer, for bonding the surface electrode to skin tissue surrounding the skin surface receiving the electrical signal.

According to still further features in the described preferred embodiments, the metal of the foil is selected from the group of metals consisting of gold and platinum.

According to still further features in the described preferred embodiments, at least one hole is disposed in the electrically conductive layer such that the surface electrode is a breathable surface electrode.

According to still further features in the described preferred embodiments, the at least partially-conductive surface layer is bio-compatible.

According to still further features in the described preferred embodiments, the artificial skin includes a polymer membrane.

According to still further features in the described preferred embodiments, the artificial skin includes a dermal layer.

According to still further features in the described preferred embodiments, the artificial skin includes polysiloxane.

According to still further features in the described preferred embodiments, the artificial skin includes a material selected from the group consisting of a nylon matrix, gelatin, polyether, polyester, silicone, polytetrafluoroethylene (-Teflon®), poly-L-lactide, cellulose, and collagen glycosamino glycan copolymers.

According to still further features in the described preferred embodiments, the at least partially-conductive surface layer includes a conductive gel.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3a is a perspective, partially exploded view of the surface electrode of the present invention;

FIG. 3b is a schematic side view of the embodiment of FIG. 3a, and

FIG. 4 is a schematic side view of another preferred embodiment, in which the surface layer of the electrode includes artificial skin and a conductive gel.

Figure 1A:
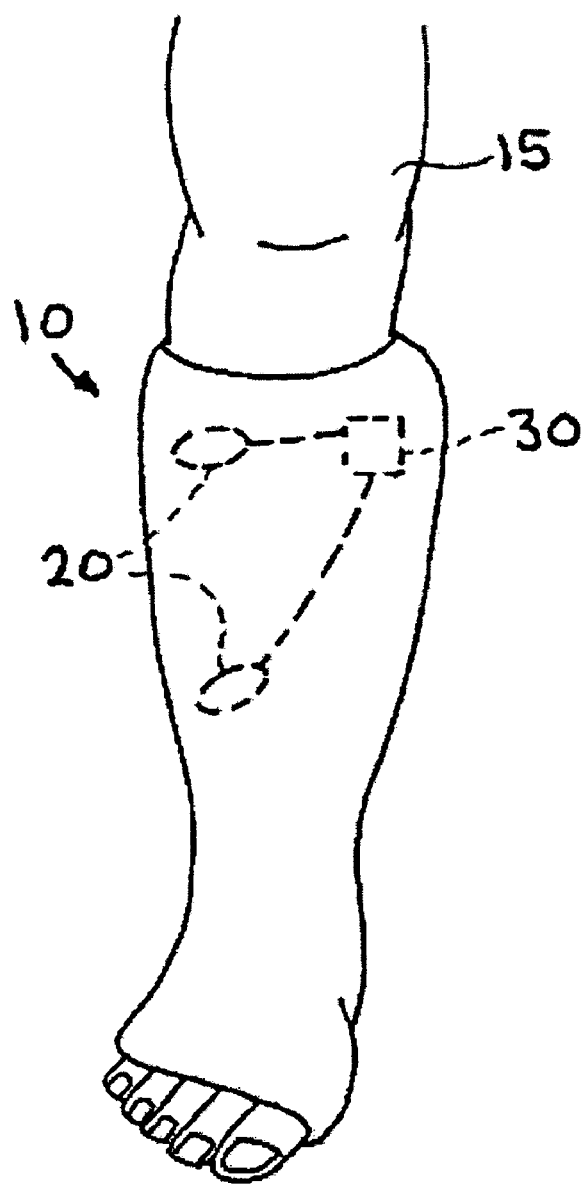
FIG. 1 shows a leg with a cast having an integrated muscle stimulation system, as disclosed in U.S. patent application No. 20020016618 to Da Silva et al.

DESCRIPTION OF THE PREFERRED
EMBODIMENTS

The present invention is a surface electrode for electrical stimulation of tissue, the electrode having sustained mechanical and electrical performance over long-term use.

The principles and operation of the electrical stimulation method according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

There are several known devices for electrical stimulation of injured tissue situated underneath a cast, including U.S. Pat. Nos. 4,398,545, 4,574,809, 4,998,532, and 6,321,119, and U.S. patent application No. 20020016618, all of which are incorporated by reference for all purposes, as if fully set forth herein.

By way of example, U.S. patent application No. 20020016618, to Da Silva, et al., teaches a device that allows electrical stimulation to an anatomical site covered by a cast. FIG. 1 shows the key components of this integrated cast and muscle stimulation device of the prior art, as the device would be used for a lower leg fracture. The cast 10 is molded around the lower leg 15 to immobilize the fracture. Replaceable electrodes 20 are positioned over superficial aspects of the peripheral nerves innervating the musculature surrounding the fracture site. An electrical stimulation unit 30 applies voltage pulses to the electrodes through buried electrical conductors (not shown).

The electrode port structure allows the placement of both an electrode module and a restraint module. In order to prevent skin from herniating into the port, either an electrode module or restraint module must be disposed within the port at all times.

Figure 2B:
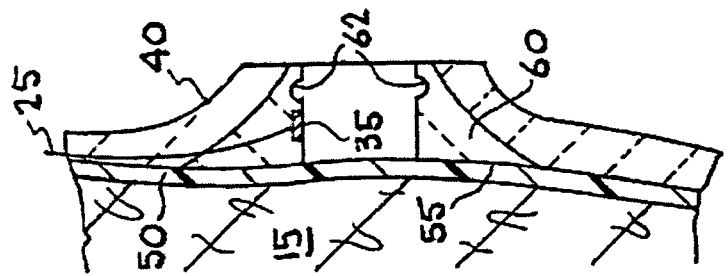
FIGS. 2A and 2B illustrate cross sectional view of the custom integration of the prior art port of FIG. 1 into the cast.
Figure 2A:
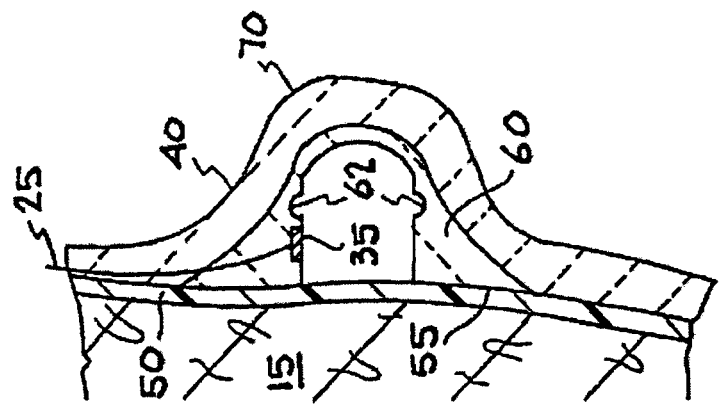

The replaceable electrodes 20 are inserted into a prepared port that is placed within the cast during the cast building phase. FIGS. 2A and 2B illustrate embodiments of how the port is integrated into the cast. First, the physician winds a layer of soft material 50 (e.g., cotton, foam, etc.) around the skin (e.g., lower leg 15) covering the broken bone. A special port structure 60 is then placed at the appropriate anatomical site for stimulation. The bottom surface of the lower section 55 could be adhesive to prevent the port structure from moving. The physician next applies the cast outer layers 40 that cover the port structure 60 and form a raised region 70 (FIG. 2A). The electrical conductor 25 connects to a conductive pad 35 that is exposed at the internal surface of the port. An indentation 62 is used to capture the electrode or restraint module. After the cast has dried and is rigid, a special saw is used to cut out the raised region producing a port as shown in FIG. 2B. The soft material 50 within the port structure can then be removed to expose the skin. The upper surface of the lower section 55 can be treated and coated with a primer to ensure bonding with the cast outer coat 40.

The port for the replaceable electrodes complicates the device in several respects. In addition to the additional equipment and fabrication requirements, the cast is intimately integrated with the muscle stimulation device. Consequently, the cost of the specialized cast is correspondingly high, and there are additional costs and procedures associated with the additional inventory requirements.

The device disclosed by U.S. patent application No. 20020016618 employs replaceable electrodes, because there is no known surface electrode characterized by sustained mechanical and electrical performance both during long-term storage and during intimate contact with human skin over the course of several weeks, and more particularly, under the difficult topical conditions underneath a cast.

By sharp contrast, the surface electrode of the present invention provides the requisite sustained electrical properties during long-term storage and during intimate contact with human skin over the course of several weeks, even in the humid and saline environment underneath a cast.

A perspective, partially exploded view of the surface electrode 100 of the present invention is provided in FIG. 3A. Surface electrode 100 includes a metal foil layer 12, for receiving an electrical signal from a power source or signal generator (not shown) via conducting wires 14. Attached to metal foil layer 12, and disposed between metal foil layer 12 and the skin surface of the patient is a thin, at least partially-conductive surface layer 16. In a preferred embodiment, surface layer 16 is a hydrophilic gel. The thickness of the hydrophilic gel in surface layer 16 is preferably 0.01–0.5 mm, more preferably 0.05–0.35 mm, and more preferably 0.08–0.25 mm.

The electrical signal received via conducting wires 14 and metal foil layer 12 is delivered to the skin surface of the patient through surface layer 16. The partially-conductive properties of surface layer 16, coupled with the extremely small thickness, result in a low and even impedance between metal foil layer 12 and the skin surface. Perhaps more significantly, the impedance between metal foil layer 12 and the skin surface is so low that the absorption of water and/or sweat, as well as distortion or partial deterioration of surface layer 16, do not significantly contribute to changes in the intensity, form, and distribution of the electrical signal delivered to the skin surface.

The thinness of surface layer 16 may compromise the tackiness thereof. Hence, for those applications in which a high degree of tackiness is requisite, the tackiness of surface layer 16 may be augmented by an adhesive bandage 18. Preferably, as illustrated in FIGS. 3A and 3B, adhesive bandage 18 is attached to a back side of metal foil layer 12, so as to cover and insulate metal foil layer 12—physically and electrically—with respect to the environment. It is generally preferable for adhesive bandage 18 to extend past the perimeter of both metal foil layer 12 and surface layer 16 in all directions, such that surface electrode 100 is adhesively connected to the skin surface, in all directions, by means of adhesive bandage 18.

It will be appreciated that various alternative constructions and dispositions of adhesive bandage 18 will be evident to one skilled in the art.

Metal foil layer 12 preferably includes at least one metal having good electrical conductivity coupled with sterile/anti-microbial properties, including, but not limited to, gold and platinum.

Preferably, metal foil layer 12 is perforated to form air-permeable regions 19. This, along with the thinness of surface layer 16, enhances the breathability of surface electrode 100.

As used herein in the specification and in the claims section that follows, the term "macroscopic", with respect to an air-permeable region, refers to an air-permeable region that is large enough to be perceived by the unaided eye, as shown in FIG. 3A.

According to another preferred embodiment of the present invention, surface layer 16 includes artificial skin. Artificial skin, in various present-day embodiments, is a combination of (human) skin cells and biodegradable polymers. A three-dimensional polymer matrix acts as a template or scaffolding on which the dermal cells grow. The polymer matrix provides a proper environment for dermal cell growth, and also gives the skin shape. The matrix is preferably dual-layered, so that the artificial skin can function much like real human skin. The underlayer is porous and designed to allow the ingrowth of human dermal cells. The outer layer is entirely synthetic and designed as a barrier against infection, water loss, and ultraviolet light. Typically, human dermal cells taken from neonatal foreskin are seeded onto the polymer matrix. The cells adhere to the matrix and are then allowed to incubate for several weeks. During this time, the cells multiply and organize themselves into functioning tissue.

Artificial skin is used as an interactive bandage to cover the wound until real skin grafts can be used to cover the wound. The artificial skin interacts with the body tissue to promote healing. Polymers used in artificial skin must be biocompatible, so that the body does not reject the tissue.

There are several products that are currently approved as temporary, interactive bandages. Advanced Tissue Sciences in La Jolla, Calif. has developed "Dermagraft-TC", an artificial skin made of a polymer membrane seeded with human cells. "Dermagraft-TC" is grown on a nylon mesh and then frozen. Freezing kills the cells, but leaves the tissue matrix and cell growth factors intact. This promotes growth of tissue around the wound. Integra Life Sciences has developed "Integra Artificial Skin", a product made of a dermal layer and a synthetic polysiloxane epidermal layer. In this case, the dermal layer interacts with the cells of the patient. Another product currently in use is "Original Biobrane", a bandaging product which consists of a nylon matrix covered with a gelatin that promotes clotting factors in the wound.

Other biodegradable polymeric matrices for use in artificial skin include polyether/polyester copolymer, silicone interwoven with polytetrafluoroethylene (Teflon®), poly-L-lactide, cellulose, and collagen glycosamino glycan copolymers. It has been found to be advantageous to combine various copolymers made of both natural and synthetic components.

Surface layer 16 can consist entirely of artificial skin, or alternatively, artificial skin can be incorporated within surface layer 16. In one preferred embodiment, illustrated in FIG. 4, an at least partially conductive gel 22 is applied to surface layer 16 such that at least a portion of the surface 24 nearest the skin surface is at least partially coated with conductive gel 22. This improves the electrical contact with the skin surface, such that the impedance is low. In addition, the artificial skin 26 within layer 16 provides a high degree of breathability to surface electrode 100, and is generally well-tolerated by the skin surface. In the event that the tissue beneath surface electrode 100 has sustained some degree of damage, the artificial skin 26 within layer 16 can actually interact with the damaged skin surface so as to promote healing. Moreover, contact between the artificial skin 26 is much less likely to result in infection, relative to surface electrodes known in the art.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A surface electrode for contacting a skin surface of a patient, the surface electrode comprising:
   (a) an at least partially-conductive surface layer for physically contacting the skin surface, and for conforming therewith, and
   (b) an electrically conductive layer, operatively connected to said partially-conductive surface layer, for communication of an electrical signal between said partially-conductive surface layer and said electrically conductive layer, wherein said at least partially-conductive surface layer is designed and configured so as to enable long-term, intimate contact with the skin surface of the patient over a continuous duration of several weeks.

2. The surface electrode of claim 1, further comprising:
   (c) an adhesive bandage, operatively connected to said electrically conductive layer, for bonding the surface electrode to skin tissue surrounding the skin surface through which said electrical signal passes.

3. The surface electrode of claim 1, wherein said electrically conductive layer includes a metal foil.

4. The surface electrode of claim 3, said metal of said foil being selected from the group of metals consisting of gold and platinum.

5. The surface electrode of claim 1, wherein said at least partially-conductive surface layer has a thickness of less than about 0.5 mm.

6. The surface electrode of claim 1, wherein said at least partially-conductive surface layer has a thickness of less than about 0.25 mm.

7. The surface electrode of claim 1, wherein said at least partially-conductive surface layer has a thickness of 0.05–0.35 mm.

8. The surface electrode of claim 1, wherein said at least partially-conductive surface layer has a thickness of 0.08–0.25 mm.

9. The surface electrode of claim 1, wherein said at least partially-conductive surface layer is a gel.

10. The surface electrode of claim 1, wherein said at least partially-conductive surface layer is bio-compatible.

11. The surface electrode of claim 1, wherein said at least partially-conductive surface layer includes an artificial skin.

12. The surface electrode of claim 11, wherein said artificial skin includes a polymer membrane.

13. The surface electrode of claim 11, wherein said artificial skin includes a dermal layer.

14. The surface electrode of claim 11, wherein said artificial skin includes polysiloxane.

15. The surface electrode of claim 11, wherein said artificial skin includes a material selected from the group consisting of a nylon matrix, gelatin, polyether, polyester, silicone, polytetrafluoroethylene (Teflon®), poly-L-lactide, cellulose, and collagen glycosamino glycan copolymers.

16. A surface electrode for contacting a skin surface of a patient, the surface electrode comprising:
   (a) an at least partially-conductive surface layer for physically contacting the skin surface, and for conforming therewith, and (b) an electrically conductive layer, operatively connected to said partially-conductive surface layer, for communication of an electrical signal between said partially-conductive surface layer and said electrically conductive layer, wherein said at least partially-conductive surface layer is designed and configured so as to enable long-term contact with the skin surface of the patient,
and wherein at least one hole is disposed in said electrically conductive layer, such that the surface electrode is a breathable surface electrode.

17. The surface electrode of claim 16, wherein said at least one hole is a plurality of holes disposed in said electrically conductive layer, such that the surface electrode is a breathable surface electrode.

18. The surface electrode of claim 16, wherein said at least one hole is a plurality of holes disposed in said electrically conductive layer, such that the surface electrode is a breathable surface electrode, and wherein at least one hole of said holes is a macroscopic, air-permeable region.

19. The surface electrode of claim 16, further comprising:
   (c) an adhesive bandage, operatively connected to said electrically conductive layer, for bonding the surface electrode to skin tissue surrounding the skin surface through which said electrical signal passes.

20. The surface electrode of claim 16, wherein said electrically conductive layer includes a metal foil.

21. The surface electrode of claim 20, said metal of said foil being selected from the group of metals consisting of gold and platinum.

22. The surface electrode of claim 16, wherein said at least partially-conductive surface layer has a thickness of less than about 0.5 mm.

23. The surface electrode of claim 16, wherein said at least partially-conductive surface layer has a thickness of less than about 0.25 mm.

24. The surface electrode of claim 16, wherein said at least partially-conductive surface layer has a thickness of 0.05–0.35 mm.

25. The surface electrode of claim 16, wherein said at least partially-conductive surface layer is a gel.

26. The surface electrode of claim 16, wherein said at least partially-conductive surface layer includes an artificial skin.

27. The surface electrode of claim 26, wherein said artificial skin includes a dermal layer.

28. The surface electrode of claim 26, wherein said artificial skin includes a polymer membrane.

29. A surface electrode for contacting a skin surface of a patient, the surface electrode comprising:
   (a) a flexible, at least partially-conductive surface layer for physically contacting the skin surface, and
   (b) an electrically conductive layer, operatively connected to said partially-conductive surface layer, for communication of an electrical signal between said partially-conductive surface layer and said electrically conductive layer, said electrical signal characterized by a signal intensity, form, and distribution,
wherein said at least partially-conductive surface layer is designed and configured so as to enable continuous long-term contact with the skin surface of the patient, and wherein an impedance of said at least partially-conductive surface layer is sufficiently low such that said intensity, said form, and said distribution of said electrical signal are substantially unaffected by a surface effect selected from the group consisting of absorption of sweat into said surface layer and partial deterioration of said surface layer.

30. The surface electrode of claim 29, further comprising:
   (c) an adhesive bandage, operatively connected to said electrically conductive layer, for bonding the surface electrode to skin tissue surrounding the skin surface through which said electrical signal passes.

31. The surface electrode of claim 29, wherein said electrically conductive layer includes a metal foil.

32. The surface electrode of claim 31, said metal of said foil being selected from the group of metals consisting of gold and platinum.

33. The surface electrode of claim 29, wherein said at least partially-conductive surface layer has a thickness of less than about 0.5 mm.

34. The surface electrode of claim 29, wherein said at least partially-conductive surface layer has a thickness of less than about 0.25 mm.

35. The surface electrode of claim 29, wherein said at least partially-conductive surface layer has a thickness of 0.05–0.35 mm.

36. The surface electrode of claim 29, wherein said at least partially-conductive surface layer has a thickness of 0.08–0.25 mm.

37. The surface electrode of claim 29, wherein said at least partially-conductive surface layer is a gel.

38. The surface electrode of claim 29, wherein said at least partially-conductive surface layer includes an artificial skin.

* * * * *